United States Patent
Lemaire et al.

(10) Patent No.: US 9,332,949 B2
(45) Date of Patent: May 10, 2016

(54) COLUMN HEIGHT SENSING FOR EXTRA-ORAL IMAGING

(75) Inventors: Jacques Lemaire, Marne la Vallee (FR); Philippe Congy, Meaux (FR)

(73) Assignee: TROPHY, Marne La Vallee (FR)

( * ) Notice: Subject to any disclaimer, the term of this patent is extended or adjusted under 35 U.S.C. 154(b) by 83 days.

(21) Appl. No.: 14/234,498

(22) PCT Filed: Aug. 5, 2011

(86) PCT No.: PCT/IB2011/002339
§ 371 (c)(1),
(2), (4) Date: Feb. 4, 2014

(87) PCT Pub. No.: WO2013/021231
PCT Pub. Date: Feb. 14, 2013

(65) Prior Publication Data
US 2014/0140482 A1    May 22, 2014

(51) Int. Cl.
*A61B 6/14*    (2006.01)
*H05G 1/02*    (2006.01)
(Continued)

(52) U.S. Cl.
CPC ............. *A61B 6/14* (2013.01); *A61B 6/4452* (2013.01); *A61B 6/547* (2013.01); *G03B 42/042* (2013.01);
(Continued)

(58) Field of Classification Search
CPC ......... H01J 37/00; H01J 37/02; H01J 37/023; H01J 37/30; H01J 37/3002; H01J 37/302; H01J 37/3023; H01J 37/304; H01J 37/3045; A61N 5/00; A61N 5/01; A61N 5/10; A61N 5/1048; A61N 5/1049; A61N 2005/0632; A61N 2005/0633; A61B 6/00; A61B 6/02; A61B 6/14; A61B 6/40; A61B 6/4007; A61B 6/4014; A61B 6/44; A61B 6/4411; A61B 6/4417; A61B 6/4429; A61B 6/4435; A61B 6/4441; A61B 6/4452; A61B 6/4458; A61B 6/4464; A61B 6/4476; A61B 6/54; A61B 6/542; A61B 6/544; A61B 6/545; A61B 6/547; A61B 6/587; G03B 42/04; G03B 42/042; G02B 27/028; G02B 27/04; H05G 1/00; H05G 1/02; H05G 1/70
USPC ........ 378/4, 20, 38, 39, 91, 95, 98, 98.5, 162, 378/163, 189–191, 193–197, 204, 205, 210, 378/901; 250/491.1, 522.1, 526; 433/25, 433/27, 29, 49, 50, 52, 72, 98, 103, 108, 433/229

See application file for complete search history.

(56) References Cited

U.S. PATENT DOCUMENTS 2,788,453 A * 4/1957 Lusted .......................... 378/96
3,808,694 A    5/1974 Hutchinson et al.
(Continued)

FOREIGN PATENT DOCUMENTS

DE    10 2005 007 938 A1    8/2006
EP            0373596 A1 *    9/2006 ............... A61B 6/00
(Continued)

OTHER PUBLICATIONS

QMED, "Spotlight on Sensors", Oct. 2010, MPMN, vol. 26, No. 8, pp. 1-2.*
(Continued)

*Primary Examiner* — Anastasia Midkiff (57) ABSTRACT

An extra-oral imaging system having a mount supported on a column that is adjustable in height, wherein the mount supports an x-ray source and at least one imaging sensor that are adjustable in height. A column base section remains stationary during height adjustment. A height sensing apparatus has a contact member that contacts a sensor element to provide a signal that is indicative of the height adjustment.

5 Claims, 11 Drawing Sheets

(51) Int. Cl.
*H01J 37/304* (2006.01)
*G03B 42/04* (2006.01)
*A61B 6/00* (2006.01)
*H01J 37/02* (2006.01)
*H01J 37/302* (2006.01)
*A61B 6/03* (2006.01)

(52) U.S. Cl.
CPC ............ *H01J 37/3045* (2013.01); *A61B 6/032* (2013.01); *A61B 6/4014* (2013.01); *A61B 6/4411* (2013.01); *A61B 6/4417* (2013.01); *A61B 6/4429* (2013.01); *A61B 6/4435* (2013.01); *A61B 6/501* (2013.01); *A61B 6/587* (2013.01); *H01J 37/023* (2013.01); *H01J 37/3023* (2013.01); *H05G 1/02* (2013.01)

(56) References Cited

U.S. PATENT DOCUMENTS

| | | | |
|---|---|---|---|
| 4,782,503 A | 11/1988 | Molitor et al. | |
| 5,870,450 A * | 2/1999 | Khutoryansky et al. | 378/197 |
| 6,118,842 A | 9/2000 | Arai et al. | |
| 6,302,580 B1 * | 10/2001 | Dwyer et al. | 378/197 |
| 6,859,521 B2 * | 2/2005 | Spahn | 378/117 |
| 7,200,952 B2 | 4/2007 | Montagnino | |
| 7,236,563 B2 | 6/2007 | Sa et al. | |
| 7,424,091 B2 | 9/2008 | Park et al. | |
| 7,469,032 B2 | 12/2008 | Walker et al. | |
| 7,478,947 B2 * | 1/2009 | Kobayashi | 378/181 |
| 2004/0190678 A1 * | 9/2004 | Rotondo et al. | 378/38 |
| 2006/0213996 A1 | 9/2006 | Crucs | |
| 2009/0195347 A1 | 8/2009 | Berres | |
| 2009/0245461 A1 * | 10/2009 | Lee | 378/38 |
| 2010/0239070 A1 * | 9/2010 | Mohr | 378/98 |
| 2011/0038454 A1 * | 2/2011 | Minnigh | A61B 6/06 378/62 |
| 2011/0142199 A1 * | 6/2011 | Kantor et al. | 378/39 |
| 2011/0249807 A1 * | 10/2011 | Dirisio et al. | 378/198 |
| 2012/0039436 A1 * | 2/2012 | Bothorel et al. | 378/11 |
| 2013/0307923 A1 * | 11/2013 | Inglese et al. | 348/36 |
| 2014/0241504 A1 * | 8/2014 | Lundstrom et al. | 378/62 |

FOREIGN PATENT DOCUMENTS

| | | |
|---|---|---|
| EP | 2 081 197 A1 | 7/2009 |
| EP | 2 130 491 A1 | 12/2009 |
| JP | 09-122118 A | 5/1997 |
| JP | 11-022349 A | 1/1999 |
| JP | 2002-360565 | 12/2002 |
| JP | 2005-173432 A | 6/2005 |
| JP | 2011-004830 A | 1/2011 |

OTHER PUBLICATIONS

Woska, Guido, "Membrane Potentiometers simplify position sensing", Aug. 2009, Hoffman + Krippner, Inc., www.hoffman-krippner.com, pp. 1-3.*

Koch, Reinhard, "The Membrane Potentiometer: A Competitive Alternative to Traditional Linear and Rotary Position Sensors", Jan. 27, 2010, Hoffman + Krippner, Inc., www.sensofoil.com, pp. 1-10.*

International Search Report for International Application No. PCT/IB2011/002339 mailed on Sep. 5, 2012, 3 pages.

* cited by examiner

COLUMN HEIGHT SENSING FOR EXTRA-ORAL IMAGING

FIELD OF THE INVENTION

The invention relates generally to the field of extra-oral dental imaging and more particularly to apparatus and methods for determining the column height prior to beginning the imaging session.

BACKGROUND OF THE INVENTION

Radiological imaging is recognized to have significant value for the dental practitioner, helping to identify various problems and to validate other measurements and observations related to the patient's teeth and supporting structures. Among x-ray systems with particular promise for improving dental care is the extra-oral imaging apparatus that is capable of obtaining a contiguous panoramic radiograph of the patient showing the entire dentition of the jaw. To obtain this type of image, a radiation source and an imaging detector, maintained at a fixed distance from each other, synchronously revolve about the patient, taking a series of images by directing and detecting radiation that is directed through the patient at different angles of revolution.

Combination systems that provide both CT and panoramic x-ray imaging have been proposed. For example, U.S. Pat. No. 6,118,842 entitled "X-RAY IMAGING APPARATUS" to Arai et al. discloses an X-ray imaging apparatus for both CT imaging and panoramic imaging. The apparatus includes an X-ray source, an X-ray detector for detecting X-rays having passed through the subject, and supporting means for supporting the X-ray source and the X-ray detector so that they are spatially opposed to each other across the subject; and mode switching means for switching between a CT mode and a panorama mode. To detect X-rays, only one large area X-ray detector is used. The X-ray imaging apparatus can obtain both types of images by switching modes during the imaging session. However, the proposed imaging apparatus performs both CT and panoramic imaging using only one detector. This requires an expensive detector capable of carrying out both imaging functions in a satisfactory manner.

Figure 1:
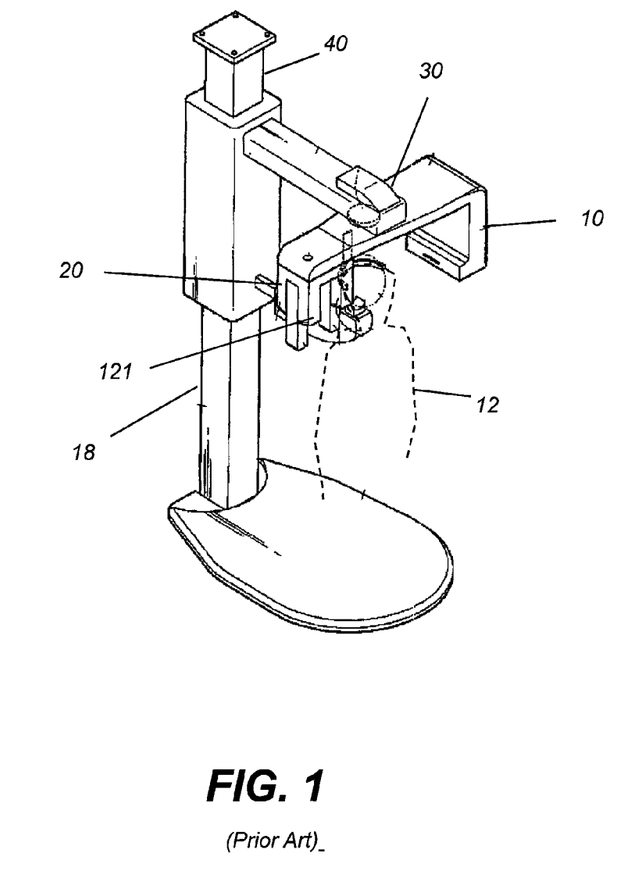
FIG. 1 is a perspective view of an extra-oral imaging apparatus.

More recently, U.S. Pat. No. 7,236,563 entitled "COMBINED PANORAMIC AND COMPUTED TOMOGRAPHY PHOTOGRAPHING APPARATUS" to Sa et al. describes a combination system that allows both CT and panoramic imaging using two separate sensors or detectors. By way of example, FIG. 1 in the present application shows an embodiment of the Sa et al. '563 imaging system, a combined panoramic and CT imaging apparatus 40. A column 18 is adjustable for height of the subject. The patient 12 or other subject, shown in dotted outline, is positioned between an x-ray source 10 and an x-ray imaging sensor panel 20. X-ray imaging sensor panel 20 rotates on a rotatable mount 30 in order to position either a CT or a panoramic sensor 121 for obtaining the exposure. For CT imaging, CT sensor 121 is positioned behind the subject, relative to x-ray source 10. The operator rotates CT sensor 121 into this position as part of imaging setup Similarly, the operator rotates panoramic sensor 121 into position behind the subject as part of the setup for a panoramic imaging session.

Another recent system combines CT, panoramic, and cephalometric imaging from a single apparatus. U.S. Pat. No. 7,424,091 entitled "COMBINED PANORAMIC, CT (COMPUTED TOMOGRAPHY) AND CEPHALOMETRIC PHOTOGRAPHING APPARATUS" to Park et al. describes such a system.

An imaging apparatus for extra-oral imaging and for imaging of teeth, bone, and various other structures of the patient's head should have some adjustability for the height of the patient. Referring to the example of FIG. 1, column 18 should be readily adjustable so that the same equipment can be used for adults or children of various heights. While height adjustment can be performed manually, there are advantages to adjustment methods that provide some amount of automation or at least mechanical assistance. In order for this capability to be provided, it is useful to have some way to measure column height. This not only serves to help automate the adjustment process, but also provides data that make it easier to repeat an imaging exam using similar parameters.

Various types of solutions have been proposed for determining the height of a telescoped column or of a component that moves up or down a column. Various types of limit switches could be employed to provide some level of information on height setting. However, limit switches can provide only range information rather than actual height. Rotary encoders and similar devices have also been proposed for obtaining height values, but may not be compatible with the mechanical actuators used.

Thus, there is a need for measurement apparatus for column height of an extra-oral imaging apparatus.

SUMMARY OF THE INVENTION

An object of the present invention is to address the need for improved column height sensing for extra-oral imaging systems. A feature of the present invention is the use of a linear potentiometer device for providing a signal indicative of a height position. Apparatus and methods of the present invention can be used in a variety of imaging system designs, including systems that use multiple columns.

Advantages of the present invention include relative simplicity of design and adaptability to different column configurations. The height sensing apparatus of the present invention is relatively unobtrusive and requires only a small amount of space.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to an embodiment of the present invention, there is provided an extra-oral imaging system, the apparatus comprising: a mount supported on a column, wherein the mount supports an x-ray source and at least one imaging sensor that are adjustable in height; a column base section that remains stationary during height adjustment; and a height sensing apparatus that comprises a contact member that contacts a sensor element to provide a signal that is indicative of the height adjustment.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

The following is a detailed description of the preferred embodiments of the invention, reference being made to the drawings in which the same reference numerals identify the same elements of structure in each of the several figures.

Where they are used, the terms "first", "second", and so on, do not necessarily denote any ordinal or priority relation, but may simply be used to more clearly distinguish one element from another. As used herein, the term "energizable" indicates a device or set of components that perform an indicated function upon receiving power and, optionally, upon receiving an enabling signal.

As used in the context of the present disclosure, the term "linear potentiometer" refers to a device that presents a variable resistance according to a linear position. The linear potentiometer of described embodiments of the present invention has an elongated sensor element that extends in the direction of the measured linear position and a contact member that contacts the elongated sensor element at a position corresponding to the measured linear position. Other types of linear potentiometer could alternately be used.

Figure 2A:
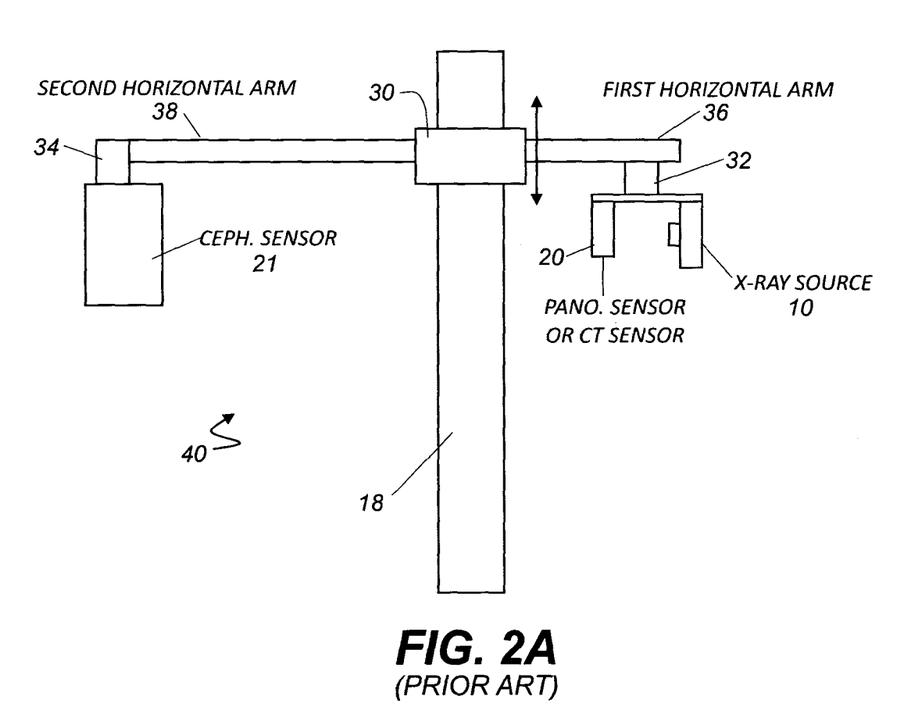
FIG. 2A is a schematic view of an extra-oral imaging apparatus having a rotatable mount on an adjustable column.

Embodiments of the present invention address the need for sensing, reporting, and recording the height setting of a column in an extra-oral imaging apparatus or other device that has an adjustable column height. FIG. 2A shows, from a side view, components of imaging apparatus 40 for extra-oral imaging having adjustable column 18 height. In this embodiment, mount 30 on column 18 is vertically movable. Both x-ray panel 20 and a cephalometric imaging sensor 21 are provided on mount 30. X-ray panel 20 and x-ray source 10 are mounted on an extension 32 suspended from a first horizontal arm 36. Cephalometric imaging sensor 21 is mounted on an extension 34 suspended from a second horizontal arm 38.

Figure 2B:
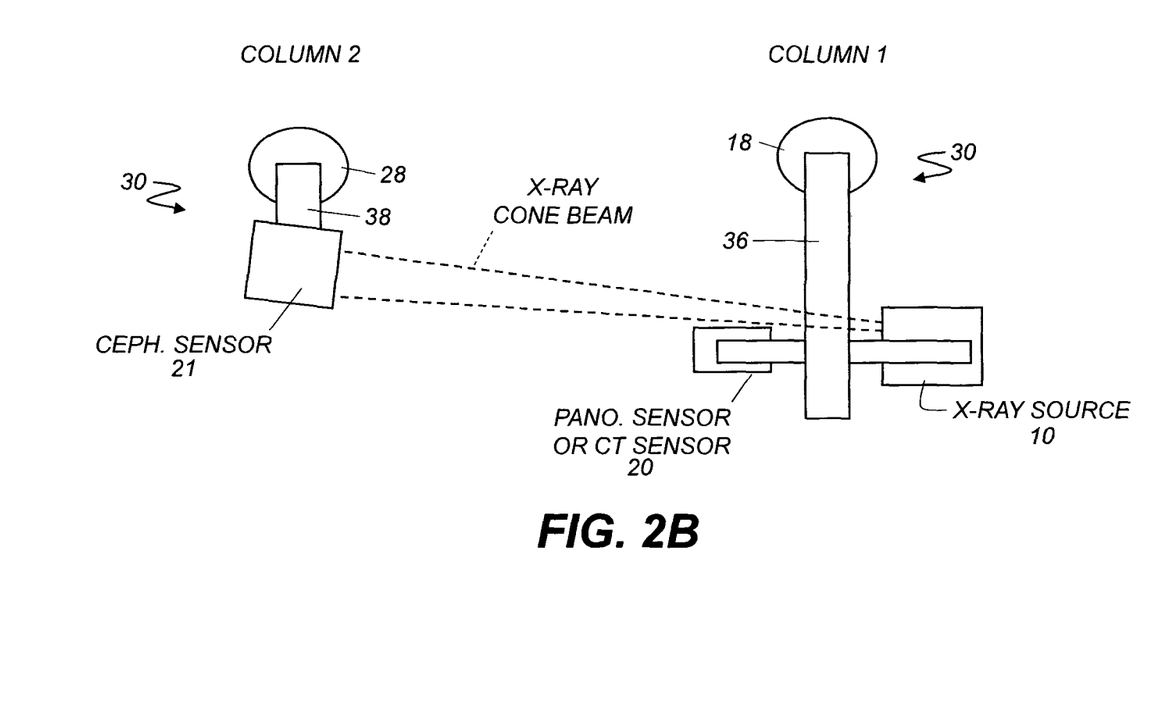
FIG. 2B is a top view of an extra-oral imaging apparatus with two separate columns having adjustable height.

The top view of FIG. 2B shows an alternate arrangement in which separate columns 18 and 28 are used, column 18 having mount 30 for the x-ray source and panoramic sensor 20, and column 28 having mount 30 for the cephalometric sensor 21. Height measurement and adjustment are also needed for this equipment arrangement, particularly to align cephalometric sensor 21 height with respect to x-ray source 10.

Figure 3:
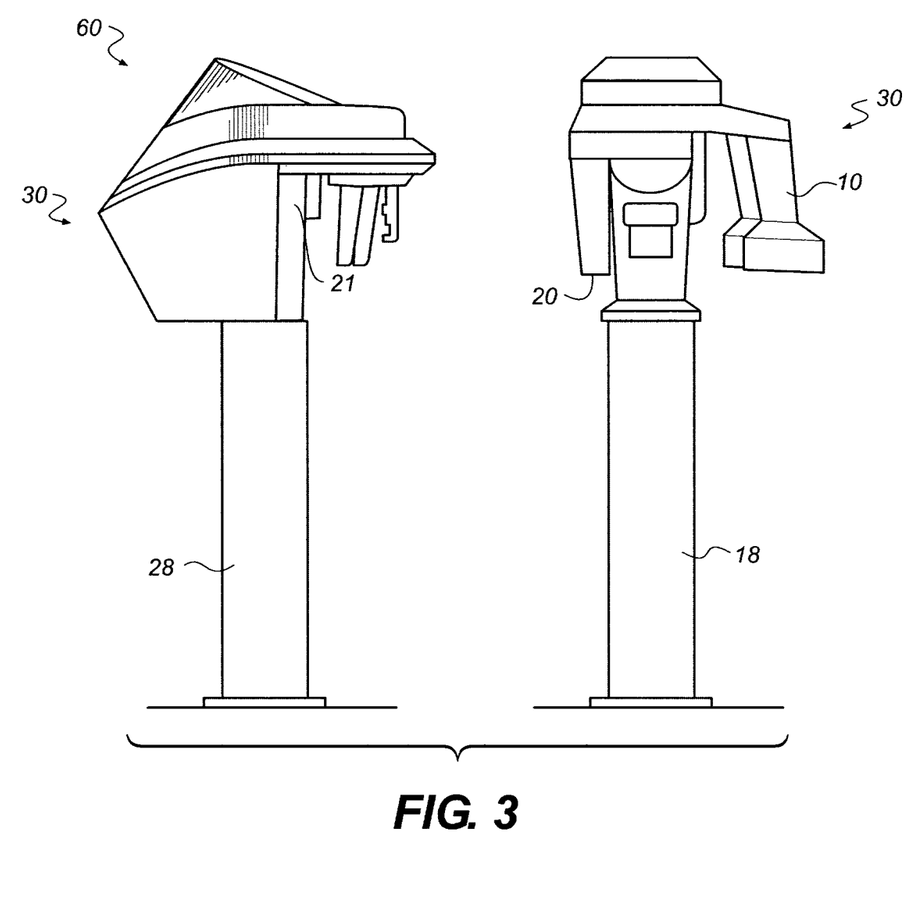
FIG. 3 is a side view of an extra-oral imaging apparatus with two separate columns having adjustable height.

FIG. 3 shows front and side views of an extra-oral imaging apparatus 60 having an adjustable column height for each of two columns 18 and 28 according to an embodiment of the present invention. In this embodiment, column 18 has panel 20 as a panoramic sensor or computerized tomography detector. Column 28 has a cephalometric sensor 21. The support mechanisms for both panel 20 and sensor 21 both have height sensing devices, as described in more detail subsequently.

Figure 4:
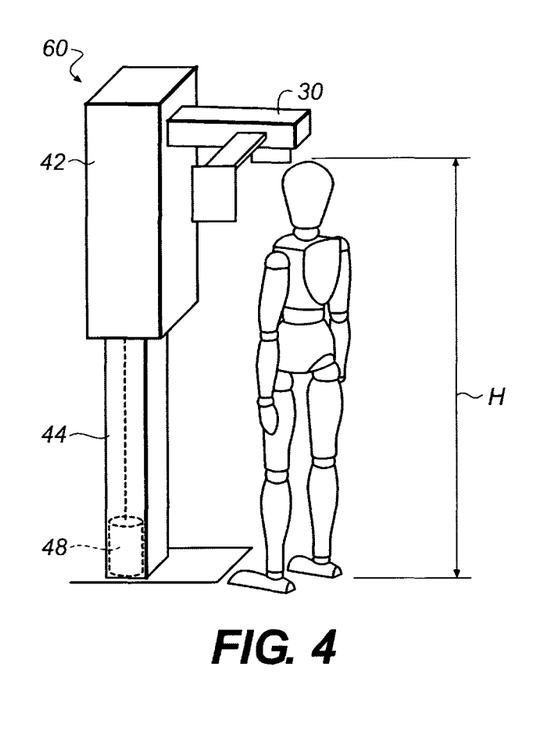
FIG. 4 is a schematic diagram that shows an imaging apparatus having adjustable column height.

FIG. 4 is a schematic diagram that shows an imaging apparatus having adjustable column height. In this embodiment, column 18 has a movable upper section 42 that includes mount 30, and a stationary lower base section 44. An optional actuator 48 provides at least some support for moving section 42 to allow adjustment to a variable patient height H.

The height-sensing components of the present invention described herein can be used for the single column configuration of FIG. 2A or, alternately, for the multi-column arrangement of FIG. 2B in which a movable section extends within a base section.

Figure 5A:
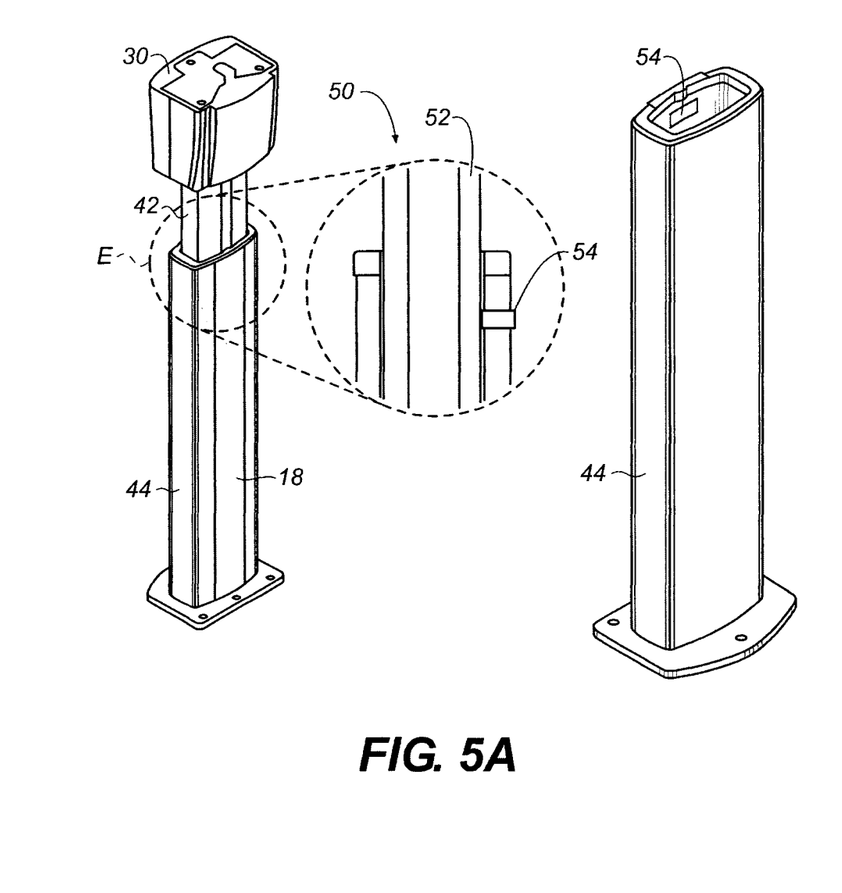
FIG. 5A is an enlarged view that shows components of a height sensing apparatus in position along a column according to an embodiment of the present invention.
Figure 5B:
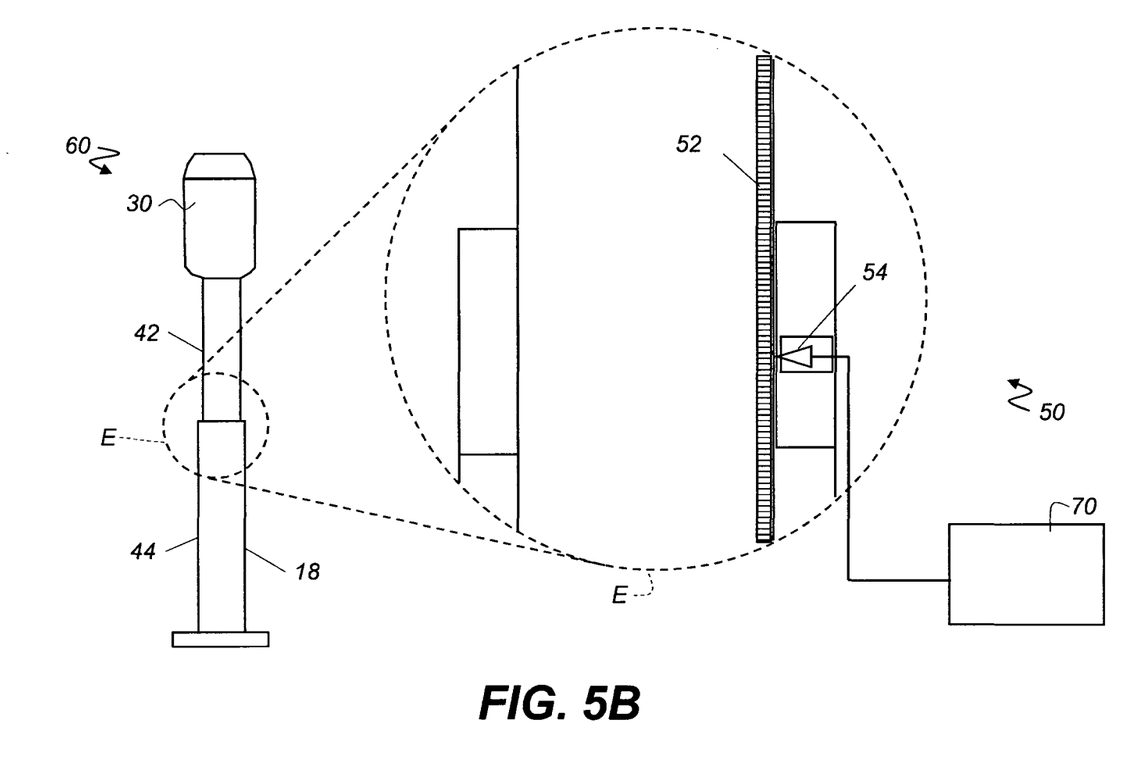
FIG. 5B is a schematic view showing components used for height sensing in the embodiment of FIG. 5A.

FIG. 5A is an enlarged view that shows components of a height sensing apparatus 50 in position along column 18 according to an embodiment of the present invention. FIG. 5B shows these components in a schematic view. A height sensing apparatus 50 has a membrane potentiometer as a sensor element 52. Coupled to one of column sections 42 or 44, sensor element 52 provides a variable voltage based on a point of contact against its surface. A finger or contact member 54 is mounted on the other section and in sliding contact against sensor element 52 to obtain a voltage signal indicative of the relative position of sections 42 and 44 as the column extends vertically or, stated alternately, of the base of column 18 and mount 30 using the arrangement of FIG. 2A. As shown in FIG. 5B, at enlargement E, contact member 54 provides a signal to a control logic processor 70 that is in signal communication with contact member 54 and with other components for display and reporting of height information. Control logic processor 70 can be any of a number of types of dedicated processor or microprocessor, for example, as well as a host computer or other device capable of executing stored electronic instructions.

Membrane potentiometers are commercially available from a number of manufacturers, such as the SENSOFOIL® Membrane Potentiometer from Hoffmann and Krippner (Switzerland) and other manufacturers. These devices come in a number of forms, but are typically designed as voltage dividers, with membrane surfaces that are spaced apart but can be forced together by the position of a sliding finger or other contact member in order to obtain a signal that relates to relative position of the contact member.

Figure 6A:
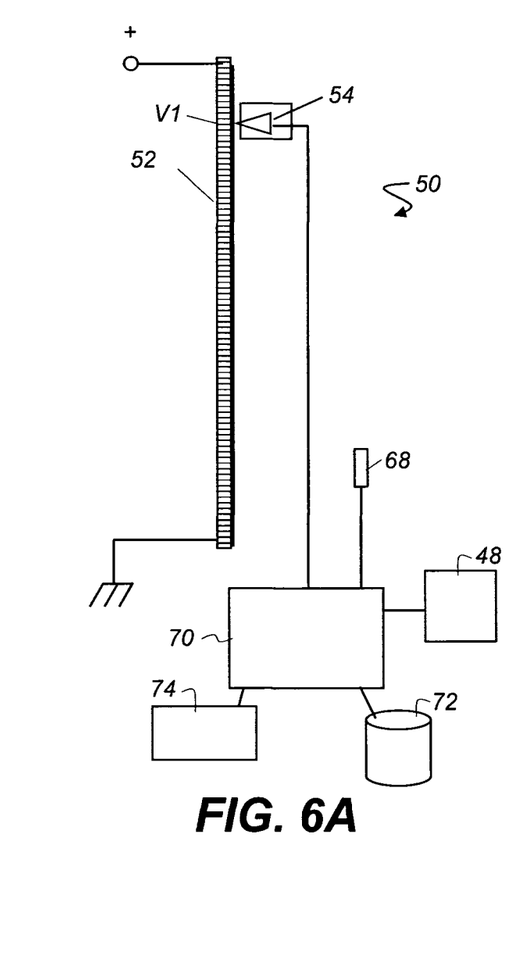
FIGS. 6A and 6B show height measurement components with height at different settings.
Figure 6B:
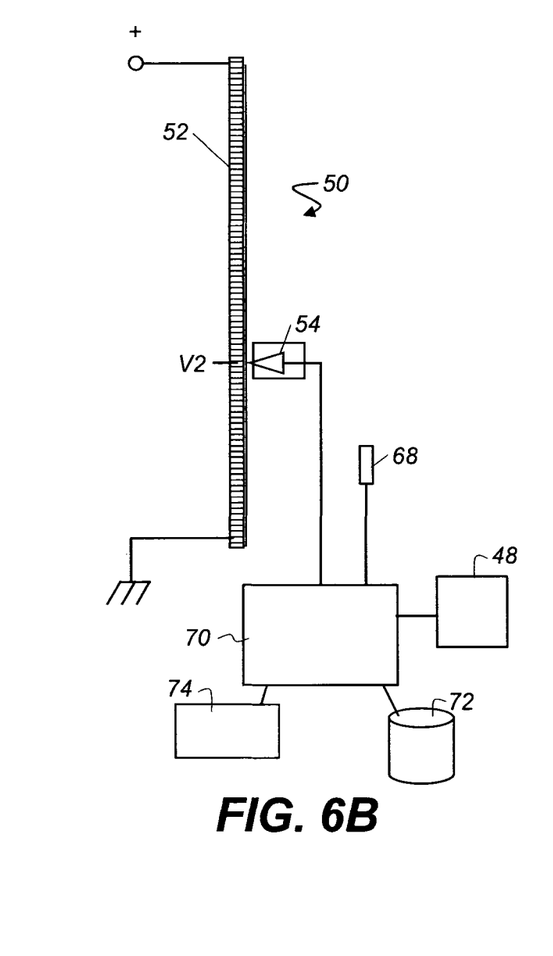

FIGS. 6A and 6B show height measurement components with height at different settings. Contact member 54 compressively contacts sensor element 52 to obtain a voltage signal V1 at one height position, at a lower column height using the arrangement of FIGS. 5A and 5B, and a different voltage signal V2 at a second height position, a higher column height in the FIG. 5A arrangement. In operation, control logic processor 70 stores the sensed voltage value or the height data it represents in a memory 72. Memory 72 can be volatile, such as random-access memory (RAM) or non-volatile, such as read-only memory (ROM) or magnetic or optical storage, for example. Control logic processor 70 is also shown in signal communication with a display 74 for indicating the height setting. Display 74 can be a numeric readout, such as an LED or LCD display, for example, or can be a display monitor that lists the height setting among other detailed information. Optional actuator 48 is controlled by an instruction signal from control logic processor 70 in one embodiment of the present invention, used to help automate height adjustment to suit each individual patient. Optional controls 68 provided on extra-oral imaging apparatus can be used to adjust height using actuator 48, while monitoring the adjustment using height sensing apparatus 50.

Figure 6C:
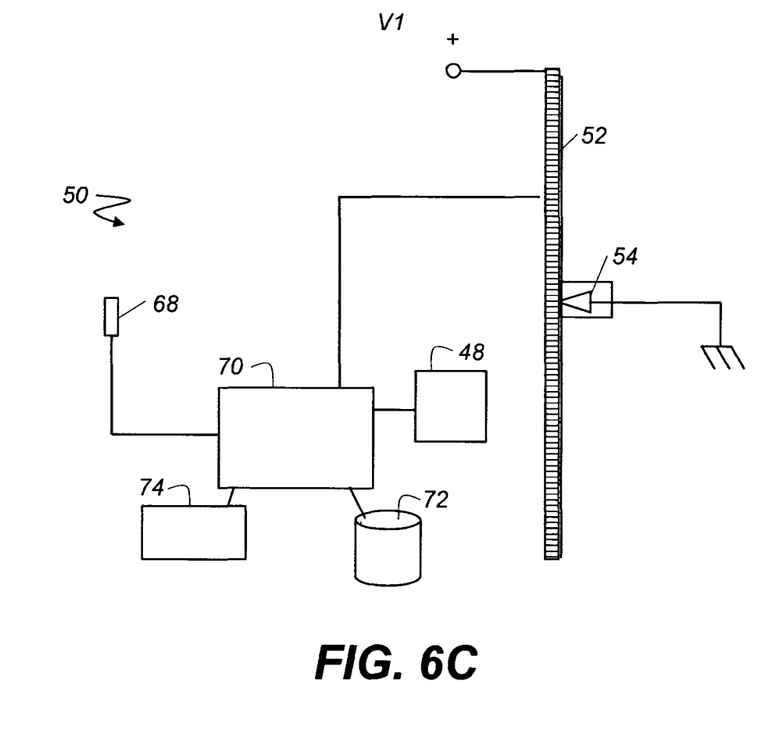
FIG. 6C is a schematic diagram that shows height sensing in an alternate embodiment of the present invention.

The signal that is indicative of column height is described as obtained from contact member 54 (or 54a, 54b) with reference to FIGS. 6A and 6B. However, it can readily be appreciated that the height signal could be obtained in other ways. For example, as shown in 6C, the height position can be determined from a signal on sensor element 52, as indicated.

Storage of height-related information for a patient, along with the images obtained and, optionally, other patient data, allows this information to be recalled and used in subsequent imaging, such as to recommend or verify appropriate height settings for an imaging session.

Sensor element 52 can be mounted on either the stationary or the movable component for height adjustment, with contact member 54 on the corresponding component, so that there is relative vertical motion between sensor element 52 and contact member 54 whenever height adjustment is made. Signal communication between contact member 54 and control logic processor 70 can be wired or wireless. In an alternate embodiment, height sensing apparatus 50 has a second sensor element 52 with a second contact member 54 for obtaining a second signal that helps to validate the first signal received.

It can be appreciated that the height measurement functions of embodiments of the present invention can be used in a number of different types of environment and for equipment having a single column that supports the x-ray head and a sensor, or two or more separate columns that must align in some way with each other. For the dual-column embodiment of FIGS. 2B and 3, actuator 48 can be used to adjust the height of components along one column for compatibility with components along another column.

Figure 7:
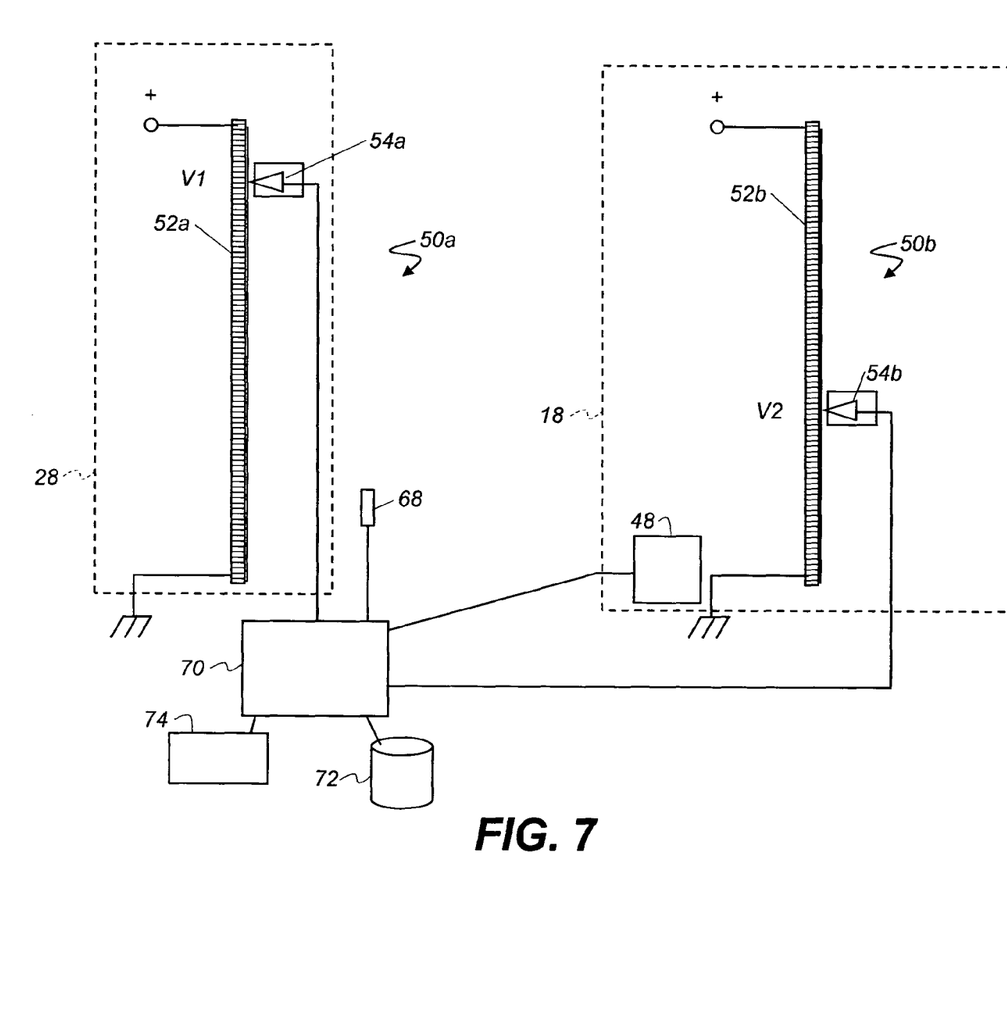
FIG. 7 is a schematic diagram showing height sensing components for a dual column embodiment.

The schematic diagram of FIG. 7 shows height sensing and adjustment components for the dual-column embodiment of FIGS. 2B and 3 according to an embodiment of the present invention. Each column has a corresponding height sensing apparatus. Column 28 uses a height sensing apparatus 50a, with a sensor element 52a and corresponding contact member 54a. Column 18 uses a height sensing apparatus 50b, with a sensor element 52b and corresponding contact member 54b. Control logic processor 70 obtains the signal from each sensor element 52a, 52b and uses the height information obtained to adjust actuator 48, shown as part of column 18 in the example embodiment of FIG. 7. As actuator 48 is adjusted, control logic processor periodically polls contact member 54b to obtain the latest signal describing height position for column 18. It can be appreciated that actuator 48 could alternately be part of column 18 or could be eliminated. Where there is no actuator 48, control logic processor displays a message or provides an audible or visual signal that indicates proper height adjustment.

Figure 8:
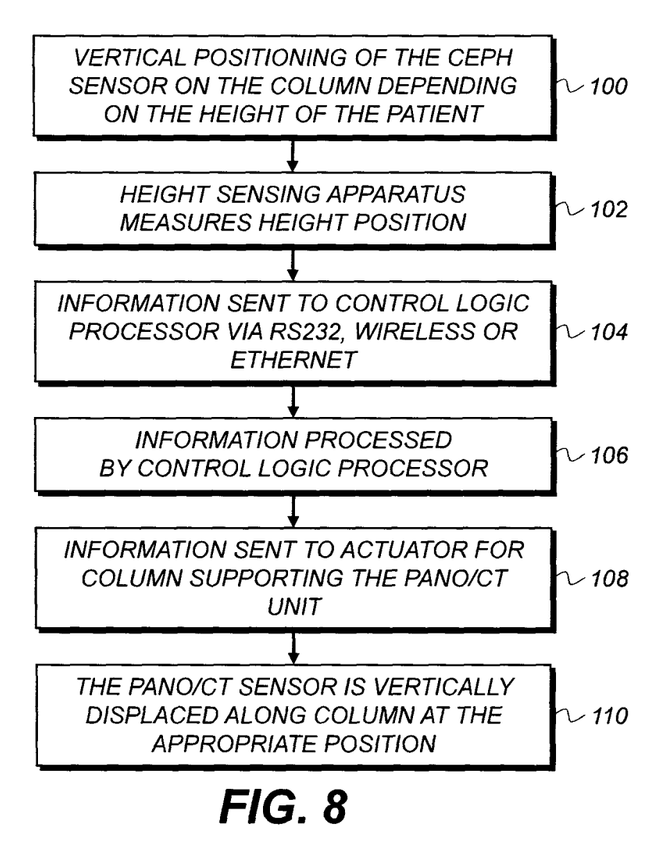
FIG. 8 is a logic flow diagram for adjustment with an actuator using the component arrangement described with reference to FIG. 7.

The logic flow diagram of FIG. 8 shows adjustment with an actuator using the component arrangement described with reference to FIG. 7. In an initial height adjustment step 100, the height along column 28 is set by the operator according to patient height. In a sensing step 102, height sensing apparatus 50a measures the height position along column 28. In a signal transmission step 104, the measurement signal is provided to control logic processor 70. In a processing step 106, the control logic checks the signal status. In an actuator drive step 108, control logic processor 70 sends an instruction signal that drives actuator 48 to change position along column 18. In a movement step 110, the sensed signal from contact member 54b is monitored to identify a termination point. According to an embodiment of the present invention, sensor 21 used for cephalometric imaging is a 2-D imaging panel; alternately, however, a line scanner could be used for obtaining this image.

It can be appreciated that the membrane potentiometer is one of a number of different possible types of sensor that could be used for providing a signal that is indicative of component height. The membrane potentiometer has advantages such as low mechanical profile, simplicity of operation, and suitability to applications for measuring linear distance. Simplicity of calibration and repeatability of measurement are additional advantages provided by the membrane potentiometer when used as sensor element 52.

While the invention has been described with reference to exemplary embodiments, it will be understood by those skilled in the art that various changes may be made and equivalents may be substituted for elements thereof without departing from the scope of the invention. Therefore, it is intended that the invention not be limited to the particular embodiment disclosed as the best mode contemplated for carrying out this invention, but that the invention will include all embodiments falling within the scope of the appended claims. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST

10. X-ray source
12. Patient
18. Column
20. X-ray sensor panel
21. Sensor
24, 26. Arm
28. Column
30. Mount
32, 34. Extension
36, 38. Arm
40. Imaging apparatus
42, 44. Section
48. Actuator
50, 50a, 50b. Height sensing apparatus
52, 52a, 52b. Sensor element
54, 54a, 54b. Contact member
60. Extra-oral imaging apparatus
68. Control
70. Control logic processor
72. Memory
74. Display
100. Initial height adjustment step
102. Sensing step
104. Signal transmission step
106. Processing step
108. Actuator drive step
110. Movement step
E. Enlargement
H. Height
V1, V2. Voltage signal

What is claimed is:
1. An extra-oral imaging system, comprising:
a first support column;
a first mount supported on the first support column, wherein the first mount supports an x-ray source and at least a first imaging sensor, wherein the relative height of the first mount is adjustable, and wherein the first support column remains stationary during height adjustment of the first mount;

a first height sensing apparatus comprising a first contact member coupled to the first mount or the first support column, the first contact member contacting a first sensor element to provide a first signal indicative of the height of the first mount;

separate, free-standing, second support column;

a second mount supported on a second support column, wherein the second mount supports a second imaging sensor, wherein the relative height of the second mount is adjustable, and wherein the second support column remains stationary during height adjustment of the second mount;

a second height sensing apparatus comprising a second contact member coupled to the second mount or the second support column, the second contact member contacting a second sensor element to provide a second signal indicative of the height of the second mount; and a control logic processor to compare the first and second signals and to provide instructions for height adjustment of one or both of the first and second mounts.

2. The apparatus of claim 1 wherein the second imaging sensor is a cephalometric sensor.

3. The apparatus of claim 1 further comprising an actuator that is energizable to adjust the height of the second mount.

4. The apparatus of claim 1 wherein the first or second sensor element is a linear potentiometer that comprises a membrane.

5. A method for sensing column height in an extra-oral imaging system, comprising:

providing a first support column;

supporting a first movable mount on the first support column, wherein the first movable mount supports an x-ray source and a first imaging sensor, and wherein the relative height of the first movable mount is adjustable relative to a first support column that remains stationary during height adjustment of the first movable mount;

providing a first height sensing apparatus comprising a first contact member that contacts a first linear potentiometer to provide a first signal indicative of the height of the first mount;

providing a separate, free-standing, second support column;

supporting a second movable mount on the second support column, wherein the second movable mount supports a second imaging sensor, and wherein the relative height of the second movable mount is adjustable relative to the second support column that remains stationary during height adjustment of the second movable mount;

providing a second height sensing apparatus comprising a second contact member that contacts a second linear potentiometer to provide a second signal indicative of the height of the second mount; and adjusting the height of one or both of the first and second movable mounts according to a comparison of the first and second signals.

* * * * *